(12) United States Patent
Roldan

(10) Patent No.: US 11,413,240 B2
(45) Date of Patent: Aug. 16, 2022

(54) METHYLENE BLUE SOLUTION FOR THE TREATMENT OF ORAL LESIONS

(71) Applicant: Board of Regents, The University of Texas System, Austin, TX (US)

(72) Inventor: Carlos Julio Roldan, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/473,214

(22) PCT Filed: Dec. 29, 2017

(86) PCT No.: PCT/US2017/068892
§ 371 (c)(1),
(2) Date: Jun. 24, 2019

(87) PCT Pub. No.: WO2018/126107
PCT Pub. Date: Jul. 5, 2018

(65) Prior Publication Data
US 2020/0093733 A1    Mar. 26, 2020

Related U.S. Application Data

(60) Provisional application No. 62/511,773, filed on May 26, 2017, provisional application No. 62/440,221, filed on Dec. 29, 2016.

(51) Int. Cl.
| | | |
|---|---|---|
| *A61K 31/5415* | (2006.01) | |
| *A61P 1/00* | (2006.01) | |
| *A61P 1/02* | (2006.01) | |
| *A61P 1/04* | (2006.01) | |
| *A61P 43/00* | (2006.01) | |
| *A61K 9/00* | (2006.01) | |
| *A61K 9/08* | (2006.01) | |
| *A61P 17/02* | (2006.01) | |
| *A61K 45/06* | (2006.01) | |
| *A61K 47/02* | (2006.01) | |

(52) U.S. Cl.
CPC ............ *A61K 9/006* (2013.01); *A61K 9/08* (2013.01); *A61K 31/5415* (2013.01); *A61K 45/06* (2013.01); *A61K 47/02* (2013.01); *A61P 1/00* (2018.01); *A61P 17/02* (2018.01)

(58) Field of Classification Search
CPC ...... A61K 9/006; A61K 9/08; A61K 31/5415; A61K 8/49; A61P 17/02; A61P 1/00; A61P 1/02; A61P 1/04; A61P 29/00; A61P 43/00; A61Q 11/00
See application file for complete search history.

(56) References Cited

U.S. PATENT DOCUMENTS

| | | | | |
|---|---|---|---|---|
| 5,611,793 A | * | 3/1997 | Wilson .................. | A61K 8/042 606/2 |
| 6,409,992 B1 | * | 6/2002 | Kleinberg ............. | A61K 8/27 424/49 |
| 2002/0168334 A1 | * | 11/2002 | Jacob .................... | A61K 47/36 424/78.31 |
| 2004/0033936 A1 | * | 2/2004 | Wulfert ................. | A61K 31/54 514/474 |
| 2006/0093561 A1 | * | 5/2006 | Kennedy .............. | A61Q 17/005 514/561 |
| 2006/0264423 A1 | * | 11/2006 | Wood ................... | A61K 31/538 514/229.8 |
| 2007/0036858 A1 | * | 2/2007 | Schneider ............ | A61J 7/0046 424/471 |
| 2007/0123520 A1 | * | 5/2007 | Wood ................... | A61P 31/16 514/224.8 |
| 2008/0031960 A1 | * | 2/2008 | Wilson ................. | A61K 33/38 514/410 |
| 2008/0312219 A1 | | 12/2008 | Brown et al. | |
| 2016/0214958 A1 | | 7/2016 | Färnegårdh et al. | |
| 2016/0296531 A1 | | 10/2016 | Wischik et al. | |

FOREIGN PATENT DOCUMENTS

| | | | | |
|---|---|---|---|---|
| CN | 103385804 A | * | 11/2013 | |
| EP | 2 138 174 | | 12/2009 | |
| WO | WO 2002-003048 | | 1/2002 | |
| WO | WO-0203048 A1 | * | 1/2002 | ............ A61K 49/006 |
| WO | WO-2014125975 A1 | * | 8/2014 | ............ A61K 31/665 |
| WO | WO 2016-106313 | | 6/2016 | |
| WO | WO-2016106313 A1 | * | 6/2016 | ............. A61Q 11/00 |

OTHER PUBLICATIONS

Mehdipour, M., et al. "A comparison between zinc sulfate and chlorhexidine gluconate mouthwashes in the prevention of chemotherapy-induced oral mucositis." Daru: Journal of Faculty of Pharmacy, Tehran University of Medical Sciences 19.1 (2011): 71-73.*
Laila, Rajesh V., et al. "MASCC/ISOO clinical practice guidelines for the management of mucositis secondary to cancer therapy." Cancer 120.10 (2014): 1453-1461.*
Dondas, A., et al. "Repeated methylene blue administration produces analgesia in experimental pain." The Journal of Headache and Pain 14.1 (2013): 1-1.*
Huynh, Nam Cong-Nhat, et al. "Rinsing with saline promotes human gingival fibroblast wound healing in vitro." PloS one 11.7 (Jul. 21, 2016): e0159843. (Year: 2016).*
Aghahosseini et al., "Methylene blue-mediated photodynamic therapy: a possible alternative treatment for oral lichen planus," *Lasers in Surgery and Medicine,* 38(1):33-38, 2006.
Cruz Éde et al., "Clinical, biochemical and histological study of the effect of antimicrobial photodynamic therapy on oral mucositis induced by 5-fluorouracil in hamsters," *Photodiagnosis and Photodynamic Therapy,* 12(2):298-309, 2015.
Dondas et al., "Repeated methylene blue administration produces analgesia in experimental pain," *J Headache Pain,* 14(Suppl 1):P86, 2013.

(Continued)

*Primary Examiner* — Bethany P Barham
*Assistant Examiner* — Peter Anthopolos
(74) *Attorney, Agent, or Firm* — Parker Highlander PLLC

(57) ABSTRACT

The present disclosure provides methods and compositions for the treatment of oral lesions in a subject comprising a methylene blue oral rinse.

20 Claims, No Drawings

(56) References Cited

OTHER PUBLICATIONS

Ferreira, "Oral mucositis and laser therapy associated with photodynamic therapy OMLTPT)," ClinicalTrials.gov, NCT02555501, 2015.

Lalla et al., "Management of oral mucositis in patients with cancer," *Dent Clin North Am.,* 52(1):61-viii, 2008.

Lalla et al., "Treatment of mucositis, including new medications," *Cancer J.,* 12(5):348-354, 2006.

Muchmore and Dahl, "One blue man with mucositis," *New England Journal of Medicine,* 327(2): 133, 1992.

PCT International Search Report and Written Opinion issued in International application No. PCT/US2017/068892, dated Feb. 23, 2018.

Peter et al., "Pharmacokinetics and organ distribution of intravenous and oral methylene blue," *Eur J Clin Pharmacol.,* 56(3):247-250, 2000.

Potting et al., "The effectiveness of commonly used mouthwashes for the prevention of chemotherapy-induced oral mucositis: a systematic review," *Eur J Cancer Care (Engl).,* 15(5):431-439, 2006.

Rengelshausen et al., "Pharmacokinetic interaction of chloroquine and methylene blue combination against malaria," *Eur J Clin Pharmacol.,* 60(10):709-715, 2004.

Rodríguez-Caballero et al., "Cancer treatment-induced oral mucositis: a critical review," *Int J Oral Maxillofac Surg.,* 41(2):225-238, 2012.

Saunders et al., "Systematic review of antimicrobials, mucosal coating agents, anesthetics, and analgesics for the management of oral mucositis in cancer patients," *Support Care Cancer,* 21(11):3191-3207, 2013. [published correction appears in *Support Care Cancer,* 23(2):601-602, 2015. Dosage error in article text].

Sonis, "Mucositis: The impact, biology and therapeutic opportunities of oral mucositis," *Oral Oncol.,* 45(12):1015-1020, 2009.

Trotti et al., "Mucositis incidence, severity and associated outcomes in patients with head and neck cancer receiving radiotherapy with or without chemotherapy: a systematic literature review," *Radiother Oncol.,* 66(3):253-262, 2003.

Walter-Sack et al., "High absolute bioavailability of methylene blue given as an aqueous oral formulation," *Eur J Clin Pharmacol.,* 65(2): 179-189, 2009.

\* cited by examiner

METHYLENE BLUE SOLUTION FOR THE TREATMENT OF ORAL LESIONS

The present application is a national phase application under 35 U.S.C. § 371 of International Application No. PCT/US2017/068892, filed Dec. 29, 2017, which claims the priority benefit of U.S. Provisional Applications Ser. No. 62/440,221, filed Dec. 29, 2016, and Serial No. 62/511,773, filed May 26, 2017, the entire contents of each application being hereby incorporated by reference.

BACKGROUND OF THE INVENTION

1. Field of the Invention

The present invention relates generally to the field of medicine. More particularly, it concerns methods and compositions for treatment of oral pain and/or lesions.

2. Description of Related Art

Oral mucositis is a debilitating sequela of treatment in cancer patients, one which affects oral intake, hygiene, treatment, and quality of life. Oral mucositis has been reported in 97% to 100% of patients receiving fractionated radiation therapy for head and neck cancer, 80% of patients receiving chemotherapy followed by stem cell transplantation, and 50% of patients receiving chemotherapy for lymphoma or solid tumors (Trotti et al., 2003).

Mucositis is caused by damage to submucosal structures leading to endothelial cell damage that results in abnormalities in mucosal epithelial growth. Mucositis is the product of a series of biological processes initiated by cellular damage that causes the early release of an inflammatory cascade that subsequently activates apoptosis. Clinically, patients manifest early with erythema and discoloration of the oral mucosa, leading to ulceration in latter stages with pain symptoms ranging from slight discomfort to allodynia preventing oral intake. In chemotherapy patients, symptoms typically begin 3 to 5 days after the initiation of treatment, with ulceration approximately 2 days later and resolution 2 weeks later. In patients who undergo radiation therapy, escalation of the cumulative dose beyond 20 Gy typically produces signs of mucositis (erythema), which progressively worsen to ulceration as the cumulative dose increases beyond 30 Gy (Rodriguez-Caballero et al., 2012). These ulcerations may last up to 4 weeks after the completion of treatment (Sonis, 2009).

In the cancer population, significant morbidity is associated with mucositis. Infection rates double in patients with mucositis during chemotherapy for solid tumors or lymphoma (Lalla and Peterson, 2006), and ulceration leading to systemic infection is a risk in these immunocompromised patients. A reduction of chemotherapy dose is twice as common after cycles in which patients had mucositis, and patients with mucositis have a 50% longer duration of hospitalization. The estimated hospitalization cost per chemotherapy cycle is $6277 for patients with oral mucositis and $3893 for those without mucositis (Elting et al., 2003).

Mucositis and the resulting pain decreases oral intake, hastening the need for supplemental nutrition via total parenteral nutrition or gastrostomy tube and thus increases the risks and subsequent morbidity and cost of malnourishment and infection.

In light of the significant debility associated with mucositis, proper treatment is critical in immunocompromised patients. Various oral preparations containing anesthetics, anti-inflammatories, antimicrobials, antiseptics, and mucosal coating agents with ingredients including chlorhexidine and iodine have been investigated for the treatment of mucositis; however, insufficient evidence prevents these from being recommended and used consistently (Potting et al., 2006; Saunders et al., 2013). Thus, there is an unmet need for a non-invasive, efficient, safe and cost-effective method to treat oral mucositis-associated pain and/or lesions.

SUMMARY OF THE INVENTION

In certain embodiments, the present disclosure provides methods and compositions for the treatment of oral lesions in a subject. In one embodiment, the present disclosure provides a method of relieving oral pain and/or treating oral lesions in a subject comprising administering an effective amount of a methylene blue oral rinse to the oral mucosa of the subject. In another embodiment, there is provided a composition comprising an effective amount of a methylene blue rinse for the treatment of oral lesions and/or pain in a subject. In some aspects, treating oral lesions comprises improving one or more aspects of a subject's oral function, such as improvement in the ability to eat, swallow, and/or talk. In some aspects, the oral lesions are associated with oral mucosal pathologies, such as oral mucosal pathologies which cause pain and/or oral lesions. In certain aspects, the oral lesions are associated with herpes virus, an aphthous ulcer (e.g., due to Behcet's or idiopathic), or herpangina. In other aspects, the oral lesions and/or pain are caused by the subject receiving a therapy, such as chemotherapy, stem cell therapy, a bone marrow transplant, or an antibody. In some aspects, the subject has pain associated with oral mucositis that is relieved by the administration of the methylene blue oral rinse. In other aspects, the subject has oral lesions due to oral mucositis that are treated by tissue repair with the methylene blue oral rinse. In particular aspects, the lesions are located in various locations of the mouth including sublingual, lips, tongue, uvula, oropharynx, palate, gums, and diffuse. In specific aspects, the subject has pain and lesions associated with oral mucositis that are treated by the administration of the methylene blue oral rinse. In specific aspects, the oral lesions are further defined as superficial oral lesions. In particular aspects, treatment or prevention of lesions can speed healing, reduce pain, delay or prevent occurrence of the lesion, and inhibit expansion, secondary infection, or other complications of the lesion.

In some aspects, the methylene blue oral rinse comprises 0.01% to 1% methylene blue, such as 0.05%, 0.25% to 0.75%, 0.05% to 0.2%, or 0.02% to 0.06% methylene blue. In certain aspects, the methylene blue oral rinse comprises 0.01%, 0.0125%, 0.02%, 0.025%, 0.05%, 0.1%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, or 1% methylene blue. In certain aspects, the methylene blue oral rinse comprises a saline solution.

In certain aspects, administering comprises performing an oral swish and spit technique. In particular aspects, the oral swish and spit technique comprises taking about 6 to 10 mL (e.g., about 7, 8, or 9 mL) of the oral rinse in the mouth and holding the oral rinse at painful sites for a period of time (e.g., 1, 2, 3, 4, 5, or more minutes) before swishing and spitting.

In some aspects, pain is measured using a numeric rating scale and/or oral functioning scale. In certain aspects, measuring an oral functioning scale comprises evaluating the subject's ability to swallow, eat, and talk. In some aspects, the pain and/or lesions are decreased by at least 50% as compared to pain and/or lesions prior to administering the methylene blue oral rinse, such as by at least 75, 80, 90, or 99%. For example, the patient may report pain at a level of 5 or greater on a 0-10 numeric rating scale, such as 6, 7, 8, 9, or 10, and the methylene blue oral rinse treatment results in the patient having a pain of 4 or less on the numeric rating scale, such as 3, 2, 1, or 0. In some aspects, the onset of the effect of the methylene blue oral rinse, such as the reduction in pain, ranges from less 2 hours to up to 12 hours, such as 1, 2, 3, 4, 5, 6, 7, 8, 9, 10, 11, or 12 hours. In particular aspects, the pain and/or lesions are essentially completely relieved.

In certain aspects, the subject has received or is undergoing chemotherapy, hematopoietic stem cell transplantation, bone marrow transplantation, and/or radiotherapy. In some aspects, the subject has cancer, such as head and neck cancer, thyroid cancer, oral cancer, salivary gland cancer, acute myelocytic leukemia, acute lymphocytic leukemia, B cell lymphoma, chronic lymphocyte leukemia, or multiple myeloma.

In some aspects, the subject is administered the methylene blue oral rinse every 48 hours, every 24 hours, every 12 hours, or every 6 hours. In particular aspects, the subject is administered the methylene blue oral rinse every 6 hours.

In additional aspects, the method further comprises administering an additional therapeutic agent. In some aspects, the additional therapeutic agent is an analgesic, such as an opiate analgesic.

In a further embodiment, there is provided an oral rinse formulation comprising methylene blue and a pharmaceutically acceptable carrier. In some aspects, the formulation further comprises an additive for stability and/or a flavoring. In certain aspects, the formulation further comprises an additional therapeutic agent, such as a corticosteroid and/or topical anesthetic.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

In certain embodiments, the present disclosure provides methods and compositions for the treatment of oral mucosa pathologies, such as pain and lesions associated with oral mucositis, comprising the administration of a methylene blue oral rinse. The inventor has found that chemical neurolysis of the oral lesion-affected areas with methylene blue used as an oral rinse is a non-invasive, efficient, safe, and cost-effective treatment method that can provide prolonged analgesia in patients with intractable pain of oral lesions, such as due to oral mucositis. The benefits of this therapy are reflected in its improvement of patients' quality of life by enabling oral feeding and/or controlling pain.

The present studies were performed on a series of patients with intractable oral mucositis-related pain despite conventional treatment with systemic opiates. Almost all patients responded well to the use of 0.05-0.1% methylene blue as a mouth rinse, demonstrating sustained analgesia over a few days to several months. The treatment was tolerated well, and overall patient satisfaction was very high. It was also demonstrated that the methylene blue rinse significantly reduced the total opioid requirement, as demonstrated by reductions in the patients' morphine equivalent daily dose scores after its use. Thus, the case series shows that methylene blue oral rinse therapy is an effective and inexpensive modality that can be used safely to palliate intractable oral pain in patients, such as patient with mucositis associated with cancer treatment, and/or repair tissue damage in oral lesions, such as mucositis lesions.

I. Methylene Blue Oral Rinse

Certain embodiments of the present disclosure provide a methylene blue oral rise composition, such as for the treatment of pain or tissue damage associated with oral lesions, such as oral mucositis or similar pathologies. The term "oral mucositis" refers to inflammation and/or destruction of the mucosal epithelium lining of the mouth cavity, including the cheeks, gums, tongue, lips, the roof or floor of the mouth. As used herein, the phrase "therapeutically effective amount" refers to an amount which provides a therapeutic benefit, wherein benefits can include, the prevention, treatment or amelioration of oral lesions, such as those associated with oral mucositis.

As used herein, "treating" or "treatment a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. In particular embodiments, treatment or prevention of lesions can speed healing, reduce pain, delay or prevent occurrence of the lesion, and inhibit expansion, secondary infection, or other complications of the lesion.

"Subject" and "patient" refer to either a human or non-human, such as primates, mammals, and vertebrates. In particular embodiments, the subject is a human.

Methylene blue (also known as methylthioninium chloride) is a monoamine oxidase inhibitor (MAOI). In particular, it inhibits the enzyme monoamine oxidase A, which breaks down serotonin in the central nervous system. Methylene blue also inhibits nitric oxide synthase and guanylate cyclase and has been shown to inhibit the aggregation of tau protein. The molecular formula of methylene blue is $C_{16}H_{18}N_3SCI$. The compound is a dark green crystalline powder at room temperature and appears blue in aqueous solution. The hydrated form has 3 molecules of water per unit of methylene blue. Methylene blue has a pH of 3 in water (10 g/L) at 25° C. (77° F.).

Although the pharmacology of methylene blue administered via the intravenous and oral (i.e., tablet) routes has been documented, the drug's administration via oral rinse has not been studied. Methylene blue when administered orally in tablet form is absorbed well from the gastrointestinal tract, with peak plasma concentration occurring in 1 to 2 hours; (Rengelshausen et al., 2004) the maximum whole blood concentration achieved by such administration is $\frac{1}{100}^{th}$ of that achieved by intravenous administration (Walter-Sack et al., 2009). Methylene blue crosses the blood-brain barrier, and there appear to be differences in tissue distribution depending on the route of administration. The intravenous route results in a higher central nervous system concentration than does the oral route (Peter et al., 2000). After distribution in the tissues, methylene blue is metabolized to leukomethylene blue Elimination of both methylene blue and its metabolite occurs through the urine and via the bile after either oral or intravenous administration. The elimination half-life is 5 to 6 hours (Peter et al., 2000).

The methylene blue oral rinse provided herein may comprise 0.25% to 0.75% methylene blue, such as 0.01% to 1% methylene blue, such as 0.01%, 0.0125%, 0.02%. 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, or 1% methylene blue, such as 0.025%, 0.05%, or 0.1% methylene blue. The oral rinse may comprise methylene blue dissolved in saline, water, vinegar, alcohol (e.g., 5-30% alcohol), or a mixture thereof. The solvent, such as water, may make up from about 90 to about 99.99% of the composition. For example, methylene blue oral rinse may be prepared by diluting 5-10 mL of commercially available 10 mg/mL (i.e., 1%) solution with 100-200 mL of water (Walter-Sack et al., 2009). The rinse may be stored at 20° C. to 25° C. (68° F. to 77° F.) but may be exposed to temperatures ranging from 15° C. to 30° C. (59° F. to 86° F.). In particular aspects, there is no need for light protection. Where alcohol-free preparations are preferred, these are best prepared under sterile conditions in order to provide preparations that can be kept without spoilage.

The methylene blue oral rinse composition may be formulated to be of sufficient strength that the quantity that a person can conveniently hold in the mouth at one time is adequate for one home care treatment, and treatment need not be carried out more frequently than every six hours, by inserting in the mouth a quantity of the rinse, suitably 2 to 10 milliliters, holding it in the mouth for a sufficient time, suitably one to two minutes, and removing the rinse, as by spitting out and such amounts of saliva as have accumulated in the mouth under the stimulating effect of the rinse. When measured with standard medicine droppers, the quantity of the rinse may be suitably 50 to 250 drops, most preferably 50 to 70 drops.

The methylene blue oral rinse may contain additional compounds such as to increase stability, enhance treatment of oral mucositis, and kill germs that cause plaque and gingivitis, and/or improve taste. These additional compounds may comprise one or more additives, buffering agents, preservatives, flavorings, chelating agents, anti-oxidants, humectants, stabilizers (including antioxidants), colorants, and other additives used in preparations administered into the oral cavity. Additional compounds could also include corticosteroids (e.g., dexamethasone), anti-histamines (e.g., diphenylhydramine), topical anesthetics (e.g., lidocaine), or anti-fungal agents (e.g., nystatin).

In some aspects, the methylene blue oral rinse in accordance with the present disclosure further comprises water and pharmaceutically acceptable excipients or additives such as one or more oils (e.g., an oil selected from the group comprising anethole, anisole, camphor, methyl salicylate, vanillin, eugenol, furaneol, linalool, menthol, thymol, cinnamaldehyde, citral, methyl butanoate, pentylbutanoate, pentylpentanoate, tea tree oil, peppermint oil, spearmint oil, pineapplemint oil and eucalyptus oil), sweetening agents (e.g., sorbitol), thickening agents (e.g., xanthan gum, carrageenan, carbomer, or HPMC (hydroxypropyl methyl cellulose)), preservative agents (e.g., sodium benzoate, methyl paraben, or propyl paraben), water, emulsifiers (e.g., polysorbate 80 (or Tween™ 80)), and/or at least one antacid (e.g., aluminum or magnesium hydroxide). It will be appreciated by persons skilled in the art that the above list of excipients and/or additives is provided merely by way of example and that various other such components may be used in the formulation of the present disclosure The compositions used as methylene blue oral rinses may have a pH of 3 to 8, such as a pH of 4 to 6.5. A preparation having a pH of less than about 3 would be likely to cause a stinging sensation. Furthermore, the preparations having a higher pH are often unpleasant to use. The preparations may be buffered as necessary to provide the appropriate pH. Appropriate buffer systems may include citrate, acetate, tromethamine and benzoate systems. However, any buffer system commonly used for preparing medicinal compositions would be appropriate. While the vehicle used generally is primarily water, other vehicles may be present such as alcohols, glycols (polyethylene glycol or polypropylene glycol are examples), glycerin, and the like may be used to solubilize the methylene blue. Surfactants may include anionic, nonionic, amphoteric and cationic surfactants, which are known in the art as appropriate ingredients for oral rinses. Procedures for choosing the optimum pH and buffering agents are well known. Other factors that affect stability in solution are also well known. For example, antioxidants may be added to reduce the rate of degradation due to oxidation.

Liquid formulations may contain additional components to improve the effectiveness of the product. For example, component(s) may be added to increase viscosity to provide improved retention on the surfaces of the oral cavity. Suitable viscosity increasing agents include carboxyalkyl, hydroxyalkyl, and hydroxyalkyl alkyl celluloses, xanthan gum, carageenan, alginates, pectins, guar gum, polyvinylpyrolidone, and gellan gums. High viscosity formulations may cause nausea in chemotherapy and radiation patients and are therefore not preferred. Gellan gums are preferred as viscosity modifying agents since aqueous solutions containing certain gellan gums may be prepared so that they will experience an increase in viscosity upon contact with electrolytes. Saliva contains electrolytes that can interact with such a gellan containing solution so as to increase their viscosity.

Flavorings that may be comprised within the methylene blue oral rinse may include peppermint, citrus flavorings, berry flavorings, vanilla, cinnamon, and sweeteners, either natural or artificial. Flavorings that are known to increase salivary electrolyte concentrations may be added to increase the magnitude of the viscosity change. The increased viscosity may promote retention of the solutions in the oral cavity and provide greater effectiveness due to increased contact time with the affected tissues.

In some aspects, antimicrobial preservatives may be components of the oral rinse formulation in cases where it is necessary to inhibit microbial growth. Suitable preservatives include, but are not limited to the alkyl parabens, benzoic acid, and benzyl alcohol. The quantity of preservative may be determined by conducting standard antimicrobial preservative effectiveness tests such as that described in the United States Pharmacopoeia.

In further embodiments, the methylene blue oral rinse may comprise one or more antibiotics such as erythromycin, azithromycin, clarithromycin, dirithromycin, roxithromycin carbomycin A, josamycin, kitasamycin, oleandomycin, spiramycin, troleandomycin, tylosin, cethromycin, ansamycin and telithromycin. Alternatively, the antibiotic may be any of the following, alone or in combination: an aminoglycoside (e.g., amikacin, gentamicin, kanamycin, neomycin, netilmicin, streptomycin, and tobramycin), a carbacephem (e.g., loracarbef), a carbapenem (e.g., ertapenem, imipenem/cilastatin, and meropenem), a cephalosporin (first generation, e.g., cefadroxil, cefazohn, and cephalexin), a cephalosporin (second generation, e.g, cefaclor, cefamandole, cefoxitin, cefprozil, and cefuroxime), a cephalosporin (third generation, e.g., cefixime, cefdinir, cefditoren, cefoperazone, cefotaxime, cefpodoxime, ceftazidime, ceftibuten, ceftizoxime, and ceftriaxone), a cephalosporin (fourth generation, e.g., cefepime), a glycopeptide (e.g., teicoplanin, and vancomycin), a penicillin (e.g., amoxicillin, ampicillin, azlocillin, carbenicillin, cloxacillin, dicloxacillin, flucloxacillin, mezlocillin, nafcillin, penicillin, piperacillin and ticarcillin), a polypeptide (e.g., bacitracin, colistin, and polymyxin B), a quinolone (e.g., ciprofloxacin, enoxacin, gatifloxacin, levofloxacin, lomefloxacin, moxifloxacin, norfloxacin, ofloxacin, and trovafloxacin), a sulfonamide (e.g., mafenide, prontosil, sulfacetamide, sulfamethizole, sulfanamide, sulfasalazine, sulfisoxazole, trimethoprim, and trimethoprim-sulfamethoxazole), a tetracycline (e.g., demeclocycline, doxycycline, minocycline, and oxytetracycline), tetracycline, and/or another antibiotic (e.g., chloramphenicol, clindamycin, ethambutol, fosfomycin, furazolidone, isoniazid, linezohd, metronidazole, nitrofurantoin, pyrazinamide, quinupristin/dalfopristin, rifampin, and spectinomycin)

Anti-fungal antibiotic agents may be of the polyene type and may be selected from the group consisting of nystatin, amphotericin B and natamycin. Further examples of antifungal compounds for use in the methylene blue oral rinse include an imidazole (e.g., miconazole, ketoconazole, clotrimazole, econazole, mebendazole, bifonazole, butoconazole, fenticonazole, isoconazole, oxiconazole, sertaconazole, sulconazole, thiabendazole and tiaconazole), a trazole (e.g., fluconazole, itraconazole, ravuconazole, posaconazole and voriconazole), an allylamine (e.g., terbenafine, amorolfine, naftifine and butenafine), or an echinocandin (e.g., caspofungin and micafungin), or any combinations thereof.

In some embodiments, the methylene blue oral rinse comprises a topical anaesthetic that may be selected from benzocaine, mepivacaine, ropivacaine, bupivacaine, lidocaine, prilocaine, procaine, cloroprocaine or tetracaine.

An anti-histamine for use in the methylene blue oral rinse may be selected from the group comprising a first generation H1 receptor antagonist, a second generation H1 receptor antagonist, a third generation H1 receptor antagonist, a H2 receptor antagonist, a H3 receptor antagonist and a H4 receptor antagonist. The first generation H1 receptor antagonist may be selected from an ethylenediamme (e.g., mepyramine or antazohne), an ethanolamine (e.g., diphenhydramine, carbinoxamine, doxylamine, clemastine or dimenhydrinate), an alkylamine (e.g., pheniramine, chlorphenamine, dexchlorphenamine, brompheniramine or triprolidine), a piperazine (e.g., cyclizine, hydroxyzine, or meclizine), or a tricyclic (e.g., promethazine, alimemazme, cyproheptadine or azatadine). The second generation H1 receptor antagonist may be azelastine, levocabastine or olopatadine. The H3 receptor antagonist may be thioperamide, clobenpropit or impromidine. The H4 receptor antagonist may be thioperamide.

II. Methods Of Treatment

Certain embodiments of the present disclosure provide methods to treat, ameliorate, or delay the onset of oral mucosa pathologies, such as oral mucositis. In one embodiment, the present disclosure provides a method of treating or preventing oral conditions such as comprising rinsing the oral cavity with the methylene blue oral rinse of the present disclosure. In a further embodiment, the present disclosure provides a methylene blue oral rinse formulation that exhibits long term stability.

The present disclosure also provides, in a further embodiment, a kit for the treatment or prophylaxis of oral lesions, such as oral mucositis, comprising a container having an amount of the methylene blue oral rinse in accordance with the present disclosure together with a set of instructions for using the oral rinse. The kit may optionally provide a cup or other container for conveniently dispensing an amount of the oral rinse from the container. Advantageously the cup may also have markings or other indicators for the convenient dispense of a measurement of a therapeutically effective dose of the oral rinse.

In one embodiment, the methylene composition is administered orally as a fluid comprising the methylene blue. The fluid can be, for example, a solution, a suspension, a paste, or a gel. In some embodiments, the fluid is held in the mouth for a recommended period of time before being discharged from the mouth.

Methods of using the formulations disclosed herein generally involve applying the formulations topically to mucosal surfaces of the oral cavity. In some aspects, the method comprises one to six applications per day, such as beginning 24 hours before chemotherapy or radiation until conclusion of treatment are made. The typical volume of the methylene blue oral rinse may be between 5-15 ml. Therapy is continued for as long as the patient is receiving radiation or chemotherapy.

Patients to be treated according to the disclosed methods and compositions include those who have oral mucositis. In addition, patients who do not have, but are at risk of developing, oral mucositis can be treated according to the present disclosure. In the latter group of patients, the treatment can inhibit, delay or prevent the development of oral mucositis. In some embodiments, the patient to be treated is a subject having cancer. In some embodiments, the subject to be treated is suffering from oral mucositis or is at risk of developing oral mucositis. In one embodiment, the patient to be treated has not been and is not currently receiving a vitamin D therapy.

Additional patients that may be treated by the present methods and compositions include patients with an oral mucosa pathology which causes oral lesions and/or oral pain. Exemplary oral mucosa pathologies include, but are not limited to, herpes virus, an aphthous ulcer (e.g., due to Behcet's or idiopathic), herpangina, burns (e.g, thermal or chemical), tooth extraction, gingivitis, or graft versus host disease. The oral lesions may also be caused by microbial (e.g., bacterial, viral or fungal) infection. In other aspects, the oral lesions and/or pain are caused by the subject receiving a therapy, such as chemotherapy, stem cell therapy (e.g., hematopoietic stem cell therapy), a bone marrow transplant, radiotherapy (e.g., radiotherapy to the head or neck), an antibody (e.g., anti-CD20 antibody, ituximab (e.g., RITUXAN®), ofatumumab (e.g., ARZERRA®), veltuzumab or ocrelizumab), or surgery (e.g., tumor resection).

In particular aspects, the methylene blue oral rinse is administered to treat superficial oral lesions, such as pain associated with superficial oral lesions. The oral rinse may be more effective when in direct contact with the lesion. A superficial lesion may be treated more effectively than a deep structure in the intermediate or basal layers of the mucoase, such as an abscess. For example, common superficial lesions of the oral mucosa, lips, and perioral region include candidiasis, recurrent herpes labialis, recurrent aphthous stomatitis, erythema migrans, hairy tongue, and lichen planus.

In some aspects, a subject having an oral lesion treated in accordance with the methods described herein is diagnosed or evaluated using the Oral Mucositis Assessment Scale (OMAS), wherein said OMAS comprises subscores: a mean mucositis score, a weighted mean mucositis score, an extent of mucositis score, and a worst site score. In specific embodiments, administration of a composition described herein to said subject results in a reduction of one or more of the mean mucositis score, the weighted mean mucositis score, the extent of mucositis score, or the worst site score of at least 1, at least 2, at least 3, at least 4, or at least 5 points, e.g., within 1, 2, 3, 4, 5, 6, or 7 days post-administration. See Sonis et al., *Cancer* 85(10):2103-2113 (1999).

Chemotherapeutic agents likely to cause oral mucositis include but are not limited to anthracyclines (such as daunorubicin, doxorubicin, pirubicin, idarubicin and mitoxantrone), methotrexate, dactinomycin, bleomycin, vinblastine, cytarabin, fluorouracil, mitramycine, etoposide, floxuridine, 5-fluorouracil, hydroxyurea, methotrexate, mitomycin, vincristine, vinorelbine, taxanes (such as docetaxel and paclitaxel), ifosfamide/eoposide, irinotecan, platinum, as well as combinations including one or more of these drugs. The risk of developing oral mucositis is markedly exacerbated when chemotherapeutic agents that typically produce mucosal toxicity are given in high doses, in frequent repetitive schedules, or in combination with ionizing irradiation (e.g., conditioning regimens prior to bone marrow transplant). The lesions induced by chemotherapeutic agents are clinically significant by about a week after treatment and the severity progresses to about day ten through twelve and begins to subside by day fourteen. Accordingly, in some embodiments, the patient to be treated is one undergoing or scheduled to undergo treatment with one or more of these chemotherapeutic agents.

Non-therapeutic radiation and/or chemical exposure, as may happen from accidents, acts of war, acts of civilian terrorism, space flights, or rescue and clean-up operations can also result in oral mucositis. In these scenarios the effects of radiation in the hematopoietic system and the gastrointestinal tract are critical. Furthermore, inflammation can be caused by conditions in the mouth itself, such as poor oral hygiene, dietary protein deficiency, poorly fitted dentures, or from mouth burns from hot food or drinks, toxic plants, or by conditions that affect the entire body, such as medications, allergic reactions, radiation therapy, or infections.

The method, in another embodiment, is provided to a subject with cancer. The subject may have any type of cancer. In certain embodiments, the subject has leukemia, lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, germ cell cancer, glioma or any other primary or solid tumor.

In other embodiments, the method is provided to a subject undergoing or planning to undergo chemotherapy. In still other embodiments, the method is provided prior to or concurrent with initiation of radiation therapy in the cancer subject. In yet other embodiments, the method comprises administering after radiation therapy. Alternatively, the method can comprise administering for the duration of radiation therapy. In one embodiment, the subject to be treated is a bone marrow transplantation patient, a stem cell transplantation patient, or a subject receiving head or neck irradiation.

In certain embodiments, the subject has received or will be receiving radiation therapy or chemotherapy. In certain embodiments, the oral mucositis is caused or is likely to result from radiation-induced toxicity in non-malignant tissue. In other embodiments, the oral mucositis is caused or is likely to result from chemical-induced toxicity in non-malignant tissue. In one embodiment, the chemical-induced toxicity is not caused by docetaxel.

According to the disclosed methods, compositions used herein can be administered to a patient prior to, concurrently with, or after a treatment that has induced or places the patient at risk of developing oral mucositis, or a combination of these approaches can be used. In an example, the composition is administered at the same time as, within 1-4 hours of, or on the same day as the treatment, and then for 1-3 (e.g., 1-2) days thereafter (e.g., 1-2 times per day). Other examples of treatment regimens are provided below.

The compositions can be administered to patients by any acceptable manner known in the art that achieved topical application to the oral mucosa, such as a gel, rinse, lozenge, cream, ointment, or patch. Also, treatment according to the present disclosure can be carried out in combination with other approaches to treating oral mucositis, including antimicrobial and palliative treatments, as is discussed further below.

Methods of assessing the efficacy of the treatment methods provided in the present disclosure can include the modified Harris mucositis-related pain assessment tool which was developed to fill the void of inadequate mucositis associated pain in existing assessment tools (Harris, 2006). The scale includes the NRS, which is one of the most widely utilized pain assessment measures in research and clinical care (Breivik et al., 2008). Its use is related to its ease of administration. It uses an 11-point scale for measuring pain intensity (0 representing no pain to 10 representing the worst possible pain).

A. Pharmaceutical Composition

Further embodiments of the present disclosure provide pharmaceutical compositions comprising the methylene blue oral rinse and a pharmaceutically acceptable excipient. The composition may also include conventional additives such as adhesive agents, antioxidants, crosslinking or curing agents, pH regulators, pigments, dyes, refractive particles, conductive species, antimicrobial agents, active agents and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the composition.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" or "pharmaceutically acceptable excipient" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

Non-limiting examples of suitable excipients, diluents, and carriers include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; carriers such as propylene glycol and ethyl alcohol, and lubricants such as talc, calcium and magnesium stearate, and solid polyethyl glycols.

Additives may be present in the compositions, such as flavoring, sweetening or coloring agents, or preservatives. Mint, such as from peppermint or spearmint, cinnamon, eucalyptus, citrus, cassia, anise and menthol are examples of suitable flavoring agents. Flavoring agents are preferably present in the oral compositions in an amount in the range of from 0 to 3%; preferably up to 2%, such as up to 0.5%, preferably around 0.2%, in the case of liquid compositions. Sweeteners include artificial or natural sweetening agents, such as sodium saccharin, sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof, which may be present in an amount in the range of from 0 to 2%, preferably up to 1% w/w, such as 0.05 to 0.3% w/w of the oral composition.

Other optional ingredients of oral aqueous compositions include humectants, surfactants (non-ionic, cationic or amphoteric), thickeners, gums and binding agents. A humectant adds body to the oral rinse formulation and retains moisture in a dentifrice composition. In addition, a humectant helps to prevent microbial deterioration during storage of the formulation. It also assists in maintaining phase stability and provides a way to formulate a transparent or translucent dentifrice. Suitable humectants include glycerine, xylitol, glycerol and glycols such as propylene glycol, which may be present in an amount of up to 50% w/w each, but total humectant is preferably not more than about 60-80% w/w of the composition. For example, liquid compositions may comprise up to about 30% glycerine plus up to about 5%, preferably about 2% w/w xylitol.

When the oral compositions are in the form of a mouth spray, it is preferred to include a film forming agent up to about 3% w/w of the oral composition, such as in the range of from 0 to 0.1%, preferably about 0.001 to 0.01%, such as about 0.005% w/w of the oral composition. Suitable film-formers include (in addition to sodium hyaluronate) those sold under the tradename Gantrez™.

B. Dosing

In the studies conducted herein, the methylene blue oral rinse composition was used topically to the mucosal tissue in the oral cavity every 6 hours. It will be appreciated that this dosing regimen is merely exemplary, and the dosing schedule can be varied according to each individual, to the severity of oral mucositis and in accord with other parameters. By way of example, the methylene blue oral rinse formulation can be applied topically to mucosal surfaces of the oral cavity, in some embodiments, one to five applications per day can begin 24 hours before chemotherapy or radiation, and may continue after the conclusion of cancer treatment or other therapy associated with mucositis. By way of another example, the methylene blue oral rinse formulation can be administered to the desired local area, one, two, three, four, five or more times per day, and treatment can begin before or concurrent with chemotherapy and/or radiation, and may cease prior to the end of chemotherapy and/or radiation or may continue after chemotherapy and/or radiation has ended.

In one embodiment, the method is for treating or preventing oral mucositis resulting from radiation or chemotherapy for cancer. The method includes the step of administering to a patient an effective amount of a solution or suspension containing the methylene blue. The solution or suspension is administered as, for example, a mouth-rinse.

In another embodiment, the method for treating or preventing oral mucositis resulting from radiation or chemotherapy for cancer includes the step of administering a solid dosage form to the oral cavity of a patient, for example, sublingually, wherein the methylene blue comes into contact with the inflamed tissue. The solid dosage form is one intended to be retained in the oral cavity and not ingested or swallowed by the patient.

Treatment according to the disclosed methods can begin prior to cancer treatment or other condition or therapy associated with oral mucositis (e.g., prophylactically, and/or 1-2 days or up to 1 week prior), at or near the same time as cancer treatment or other therapy associated with oral mucositis (e.g., simultaneously with, within 1-4 hours of, or on the same day as the treatment), or shortly after the cessation of cancer treatment or other condition or therapy associated with oral mucositis (e.g., within 1-4 days of cessation, and/or prior to or upon appearance of symptoms). Treatment can then be maintained, for example, until any symptoms of oral mucositis have substantially cleared or the risk of developing such symptoms has passed. Thus, treatment started before or at or near the same time as cancer treatment or other condition or therapy associated with oral mucositis can be maintained, e.g., for 1-3, e.g., 1-2 days.

In other examples, treatment is maintained for 1-4 or 2-3 weeks following the cessation of cancer treatment or other therapy associated with oral mucositis, as determined to be appropriate by one of skill in the art. In specific examples, the treatment according to the present disclosure is carried out only prior to cancer treatment or other therapy associated with oral mucositis; prior to and concurrently with cancer treatment or other therapy associated with oral mucositis; prior to, concurrently with, and after cessation of cancer treatment or other therapy associated with oral mucositis; concurrently with cancer treatment or other therapy associated with oral mucositis only; concurrently with and after cessation of cancer treatment or other therapy associated with oral mucositis only; after cessation of cancer treatment or other therapy associated with oral mucositis only; or prior to and after cessation of cancer treatment or other therapy associated with oral mucositis only. Further, treatment according to the methods of the present disclosure can be altered, stopped, or re-initiated in a patient, depending on the status of any symptoms of oral mucositis. Treatment can be carried out at intervals determined to be appropriate by those of skill in the art. For example, the administration can be carried out 1, 2, 3, 4 or more times/day. It will be appreciated that the patients to be treated with the methods described herein are not limited to cancer patients, but include any patient that is at risk of or has developed oral mucositis.

C. Combination Therapies

The methods presently disclosed can be used alone or in conjunction with other approaches to treating oral lesions, such as reducing the severity of oral mucositis.

In some embodiments, the subject is concurrently treated with at least one therapeutic agent. In some embodiments, the therapeutic is a pain reliever or a chemotherapeutic. In some embodiments, the therapeutic agent is an anti-inflammatory or antibiotic. In some embodiments, the pain reliever is a topical anesthetic selected from, but not limited to, the group consisting of fentanyl, hexylresorcinol, dyclonine hydrochloride, asbenzocaine and phenol. In some embodiments, the administering comprises administering to a subject undergoing or planning to undergo chemotherapy. In some embodiments, the administering is prior to or concurrent with initiation of radiation therapy in the cancer subject. In some embodiments, the administering is after radiation therapy. In some embodiments, the administering continues for the duration of radiation therapy. In some embodiments, the administering continues for longer than the duration of radiation therapy. In some embodiments, the administering continues for a time shorter than the duration of radiation therapy. In some embodiments, the administering comprises administering more than once daily. In some embodiments, the administering comprises administering once daily.

The other therapy may comprise anti-inflammatory agents, antibacterial agents (i.e., penicillins, cephalosporins, tetracyclines, or aminoglycosides), antifungal agents (i.e., nystatin or amphotericin B), antiviral agents (i.e., acyclovir), topical antiseptics (i.e., povidone-iodine), analgesics (i.e., lidocaine or benzocaine), or steroids (i.e., triamcinolone or hydrocortisone).

In some embodiments, the disclosed methods can be carried out in combination with antimicrobial or antifungal therapies, e.g., therapies involving administration of antibiotics such as nystatin, amphotericin, acyclovir, valacyclovir, clotrimazole, and fluconazole. As a specific example of such treatment, patients with head and neck cancer receiving radiotherapy have colonization of the oropharyngeal region with gram-negative bacteria. Selective decontamination of the oral cavity with anti-microbial agents has the benefit of reducing oral mucositis associated with radiation therapy, but there may be limitations to the beneficial effects of such treatment. Anti-microbial therapy can kill bacteria, but cannot reduce endotoxin, and indeed may actually increase endotoxin. As endotoxin is a potent mediator of inflammation, it may contribute to the aggravation of mucositis and, thus, co-treatment with an antiendotoxin compound (e.g., a Lipid A analog, such as eritoran) and antibiotics can be used as a more effective approach to treating oral mucositis in such patients, according to the present disclosure.

Other treatment strategies for oral mucositis may be combined with the methylene blue oral rise provided herein. For example, current strategies include ice chips to reduce pain and inflammation, and analgesics to manage pain, including mucosal coating mixtures that may contain topical anesthetics and antibiotics to control the opportunistic infection. Agents capable of reducing mucous absorption of the chemotherapy drugs (for example cryotherapy, allopurinol or pilocarpine) can be used, as well as agents which reduce the changes in epithelial proliferation (for example beta-carotene, glutamine or silver nitrate) or anti-inflammatory and antimicrobial agents (for example, mesalazine and/or chlorhexidine). Agents which protect the mucosa (for example, sodium bicarbonate), anaesthetic or analgesic agents (for example, lidocaine, morphine and the derivatives thereof), and agents which accelerate the healing process (for example, vitamin E, tretinoin, laser therapy etc.) or special diets and/or specific oral hygiene regimens may also be employed. The only currently approved therapeutic for oral mucositis is Kepivance™ which is the known mitogenic protein keratinocyte growth factor (KGF) that must be administered intravenously. Kepivance™ is approved for a single indication which comprises only 4% of the total oral mucositis population, i.e., treatment of oral mucositis resulting from pre-conditioning regimens (chemotherapy and radiation) in stem-cell transplant patients. Analgesics such as lidocaine oral rinses are effective for short periods of time but within hours the pain and discomfort usually returns.

In addition, a variety of oral rinses have been previously described and reported to having mixed actions against mucositis. These oral rinses may be combined with the methylene blue oral rinse of the present disclosure. Such oral rinses typically include benzydamine hydrochloride, corticosteroids and chamomile. Formulations such as those disclosed in U.S. Pat. Nos. 5,635,489, 4,961,926 and 5,102,870 describe the use of growth factors and stimulation factors such as granulocyte-macrophage colony stimulating factor and granulocyte-colony stimulating factor. Further attempts at treatment and or prophylaxis of mucositis include the use of nucleoside derivatives which can be formulated into lozenges or oral rinses and the like to coat the oral cavity or other mucosal areas such as disclosed in U.S. Patent Publication No. 2003/0236217. Other formulations include tetracycline as disclosed in U.S. Pat. No. 6,946,118, hyaluronic acid, glycyrhetinic acid and polyvinylpyrolidone in mixture with excipients and adjuvants as disclosed in U.S. Pat. No. 6,828,308, the use of an anti-microbial peptide, preferably protegrin, applied topically which has broad spectrum antimicrobial activity, good stability and adheres well to all mucosa as disclosed in U.S. Pat. No. 6,025,326, the use of glutamine as disclosed in U.S. Pat. No. 5,545,668 and the use of triclosan as disclosed in U.S. Pat. No. 5,945,089.

The methods presently disclosed can also be used in conjunction with palliative therapies including the use of topical rinses, gels, or ointments that include lidocaine, articaine, and/or morphine, as well as other analgesic or anti-inflammatory agents. Specific examples of other agents and approaches that can be used in combination with the methylene blue oral rinse, according to the methods presently disclosed, include the following: palifermin (recombinant keratinocyte growth factor; rHuKGF; Kepivance™; Amgen) and AES-14 (uptake-enhanced L-glutamine suspension) (Peterson, *J. Support Oncol.* 4(2 Suppl. 1)9-13, 2006); oral cryotherapy, low-level laser therapy, chlorhexidine, amifostine, hematologic growth factors, pentoxifylline, and glutamine (Saadeh, *Pharmacotherapy* 25(4):540-554, 2005); amifostine, antibiotic paste or pastille, hydrolytic enzymes, ice chips, benzydamine, calcium phosphate, honey, oral care protocols, povidone, and zinc sulphate (Worthington et al., *Cochrane Database Syst. Rev.* 2:CD000978, 2006); flurbiprofen (e.g., administered as a tooth patch; Stokman et al., *Support Care Cancer* 13(1):42-48, 2005); diphenhydramine, magnesium hydroxide/aluminum hydroxide, nystatin, and corticosteroids (Chan et al., *J. Oncol. Pharm. Pract.* 11(4):139-143, 2005); oral transmucosal fentanyl citrate (e.g., administered in the form of a lozenge; Shaiova et al., *Support Care Cancer* 12(4):268-273, 2004); clonazepam (e.g., in the form of a tablet; Gremeau-Richard et al., *Pain* 108(102):51-57, 2004); capsaicin (e.g., in the form of a lozenge; Okuno et al., *J. Cancer Integr. Med.* 2(3):179-183, 2004); ketamine (e.g., in the form of an oral rinse; Slatkin et al., *Pain Med.* 4(3):298-303, 2003); and granulocyte-macrophage colony-stimulating factor (GM-CSF)/granulocyte colony-stimulating factor (G-CSF), laser light therapy, and glutamine supplements (Duncan et al., *Aliment. Pharmacol. Ther.* 18(9):853-874, 2003).

III. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Methylene Blue for the Treatment of Intractable Pain Associated with Oral Mucositis Patients undergoing cancer therapy were seen for intractable pain related to oral mucositis. The primary complaint of all patients was oral pain compromising structures, which included the tongue and inner lips as well as the sublingual and oral mucosa. All patients expressed difficulty eating because it exacerbated their pain. They also reported weight loss as a result of decreased oral intake. Patients 1 and 2 were hospitalized for pain and failure to thrive, patient 3 was seen for a requested consultation in the emergency department, and patients 4 and 5 were seen in the outpatient clinic (Table 1). All 5 patients reported suboptimal pain control despite systemic therapy with opiates.

The safety checkpoints included an assessment of documented drug allergies, medications the patients were taking, and laboratory test results (including renal function and hemoglobin levels). The risk of bronchial aspiration was also assessed based on cognitive status, ability to understand and follow the recommendations, and, if available, results of a swallowing test by a speech pathologist. After these safety checkpoints were reviewed, all 5 patients were offered and agreed on the following care.

A mix of 0.05% methylene blue dilution in normal saline 100 mL total, was prepared. Patients were instructed to take a mouthful of the mix, hold it at the painful sites for 5 minutes, and then gargle and spit. These steps were to be repeated every 6 hours as needed for pain for a total of 3 to 6 uses.

All patients demonstrated an understanding of the instructions; however, varied dosing was noted. Patient 1 performed the rinsing sporadically over 4 days. Patients 4 and 5 each had an interval of more than 1 day between the first and second use to avoid the transient blue discoloration of the mouth during work. The onset of pain relief also varied among patients. Patients 1, 2, and 5 had rapid pain relief with their first use, whereas patients 3 and 4 did not experience relief until the second dose.

TABLE 1

Basic demographics, morphine equivalent daily dose, symptoms, duration, and Numeric Analog Pain Score of patients with oral mucositis before and after treatment with methylene blue oral rinse.

| Patient No. | Age | Sex | Cancer Type | Treatment | MEDD Before MB | MEDD After MB | Symptoms' Duration Before MB | MB Onset of Action | Numeric Analog Pain Score (0 to 10) Before MB | Numeric Analog Pain Score (0 to 10) At 3 Weeks Follow-Up |
|---|---|---|---|---|---|---|---|---|---|---|
| 1 | 47 | M | AML | SCT, chemotherapy | 210 | 60 | 3 weeks | 2 hours × 5 uses | 8 | 2 |
| 2 | 69 | M | AML | IT chemotherapy | 115 | 10 | 3 weeks | 2 hours × 6 uses | 7 | 0 |

TABLE 1-continued

Basic demographics, morphine equivalent daily dose, symptoms, duration, and Numeric Analog Pain Score of patients with oral mucositis before and after treatment with methylene blue oral rinse.

| Patient No. | Age | Sex | Cancer Type | Treatment | MEDD Before MB | MEDD After MB | Symptoms' Duration Before MB | MB Onset of Action | Numeric Analog Pain Score (0 to 10) Before MB | Numeric Analog Pain Score (0 to 10) At 3 Weeks Follow-Up |
|---|---|---|---|---|---|---|---|---|---|---|
| 3 | 21 | F | Sarcoma | Chemotherapy | 102 | 50 | 6 months | 12 hours × 2 uses | 8 | 0 |
| 4 | 41 | F | Salivary gland SCC | Radiation | 62 | 0 | 3 months | 12 hours × 2 uses | 5 | 0 |
| 5 | 56 | M | SCC (tonsils) | Radiation | 125 | 0 | 3 months | 1 hour × 4 uses | 8 | 2 |

AML, acute myeloid leukemia;
F, female;
IT, intrathecal;
M, male;
MB, methylene blue;
MEDD, morphine equivalent daily dose;
SCC, squamous cell carcinoma;
SCT, stem cell transplant.

At the 3-week follow-up visits, all patients reported a sustained decrease of more than 50% in their pain scores. Patients 2, 3, and 4 reported complete relief of the mucositis-related pain. Three patients were still using opiate analgesics: patient 1 for odontalgia that was unrelated to her mucositis and later addressed by a dentist and patient 2 for unresolved uvular pain resulting from a soft tissue abscess that was treated with antibiotics. Patient 5 requested continuation of the methylene blue therapy since the mix was providing complete pain relief (i.e., scores of 0 to 2 compared with a pretreatment score of 8 on a pain scale of 0 to 10 Numeric Analog Pain) lasting 6 hours. No complications were reported by any patient, although 3 reported transient blue discoloration as the main side effect.

Thus, this study demonstrated that oral rinse with diluted methylene blue is an alternative method for treating patients with intractable pain associated with oral mucositis. This case series showed that the duration of the analgesic effect can be substantially extended.

To validate the results, additional patients were assessed after methylene blue oral rinse use at the different concentrations including 0.025%, 0.05%, and 0.1% methylene blue. Table 2 shows data collected from patients who received MB oral rinse. Patients had lesions in various locations of the mouth including sublingual, lips, tongue, uvula, oropharynx, palate, gums, and diffuse.

TABLE 2

Evaluation of pain before treatment and after methylene blue oral rinse treatment.

| case | Age/G | cancer | TX | location | Length | Pre-MB | Post-MB | onset | MB % | Side effects/comments |
|---|---|---|---|---|---|---|---|---|---|---|
| 1 | 41F | Sal gland | R | SL | 3 M | 5 | 0 | 2 D | 0.05 | None |
| 2 | 69M | AML | ITC | L, T | 3 W | 8 | 0 | 2 H | 0.05 | None |
| 3 | 47M | AML | C | M, T | 3 D | 8 | 2 | 2 H | 0.05 | Burning sensation |
| 4 | 21F | Sarcoma | C | U, OP | 6 M | 5 | 0 | 8 H | 0.05 | None |
| 5 | 56M | Tonsil | R | SL | 3 M | 5 | 2 | <2 H | 0.05 | None |
| 6 | 68M | AML | C | P, SL | 4 M | 8 | 0 | <2 H | 0.05 | Shirt stain |
| 7 | 61M | AML | C | SL | 4 W | 10 | 2 | 12 H | 0.05 | None |
| 8 | 82M | MM | C | P, SL | 10 D | 7 | 3 | 2 H | 0.05 | None |
| 9 | 22M | B cell L | Sct | G | 3 D | 8 | 4 | 2 H | 0.05 | None |
| 10 | 56M | CML | C | T | 4 M | 8 | 2 | 12 H | 0.05 | None |
| 11 | 52F | Pharynx | R | D | 6 D | 8 | 4 | 6 H | 0.025 | Transient dental stain |
| 12 | 35F | CML | C | P, T | 2 M | 6 | 1 | <2 H | 0.025 | None |
| 13 | 56F | AML | C | OP | 3 W | 7 | 1 | 2 H | 0.025 | None |
| 14 | 33M | MM | Sct | D | 2 W | 5 | 1 | <2 H | 0.025 | None |
| 15 | 21F | AML | C | P, SL | 1 M | 8 | 2 | 2 H | 0.025 | None |
| 16 | 78F | MM | C | T | 3 W | 7 | 0 | 12 H | 0.1 | None |
| 17 | 62M | AML | C | G, T | 12 D | 8 | 2 | 2 H | 0.1 | None |
| 18 | 51M | AML | C | SL | 1 M | 8 | 0 | 6 H | 0.1 | None |
| 19 | 35F | ALL | C | P, OP | 2 W | 7 | 0 | 2 H | 0.1 | Transient Blue urine/feces |
| 20 | 19F | AML | C | L, SL | 2 M | 7 | 0 | 6 H | 0.1 | None |
| 21 | 38M | Larynx | C | P, OP | 4 W | 6 | 1 | <2 H | 0.05 | None |
| 22 | 28F | AML | C | SL, P | 5 D | 10 | 0 | <2 H | 0.05 | None |
| 23 | 55F | L | Sct | P, OM | 2 W | 10 | 4 | <2 H | 0.025 | None |
| 24 | 41F | L | C | OM | 4 D | 7 | 0 | <2 H | 0.025 | None |
| 25 | 61M | MM | Sct | OP, P | 7 D | 10 | 3 | <2 H | 0.1 | None |
| 26 | 69M | B cell L | C | P | 7 D | 7 | 5 | <2 H | 0.1 | None |
| 27 | 50M | Tongue | R | T, P | 8 W | 9 | 8 | 6 H | 0.05 | Minimal pain relief |
| 28 | 55M | Tongue | CR | P | 2 W | 7 | 2 | <2 H | 0.025 | None |
| 29 | 71M | L | C | L, OM, P | 4 W | 6 | 4 | <2 H | 0.05 | None |

TABLE 2-continued

Evaluation of pain before treatment and after methylene blue oral rinse treatment.

| case | Age/G | cancer | TX | location | Length | Pre-MB | Post-MB | onset | MB % | Side effects/comments |
|---|---|---|---|---|---|---|---|---|---|---|
| 30 | 53M | MM | Sct | P | 2 w | 5 | 2 | 12 h | 0.025 | None |
| 31 | 53M | MM | Sct | OM | 3 D | 7 | 2 | <2 H | 0.025 | None |
| 32 | 73F | MDS | C | P, T | 1 W | 9 | 0 | 1 W | 0.05 | None |
| 33 | 61F | L | C | T, OP | 1 W | 10 | 0 | 8 H | 0.05 | None |
| 34 | 64F | AML | C | OM | 2 W | 7 | 2 | <2 H | 0.1 | None |
| 35 | 65M | MDS | Sct | OM | 1 W | 8 | 8 | NA | 0.1 | None |
| 36 | 54M | Pharynx | R | OM, T | 2 D | 8 | 1 | 2 D | 0.025 | None |
| 37 | 55F | T | CR | T, OM | 2 D | 10 | 6 | 2 D | 0.05 | Able to eat after using it 2 days |
| 38 | 39F | AML | C | OM | 1 W | 10 | 6 | 2 D | 0.05 | None |
| 39 | 70M | Tongue | CR | P, T, OP | 2 W | 10 | 6 | 2 D | 0.05 | None |
| 40 | 70M | Tongue | CR | T | 2 W | 7 | 2 | <2 H | 0.025 | None |
| 41 | 62M | Tongue | R | T | 1 M | 10 | 0 | <2 H | 0.025 | None |
| 42 | 64F | Tongue | CR | OM | 2 M | 10 | 5 | 6 H | 0.1 | None |
| 43 | 63F | MM | Sct | OM | 1 W | 8 | 0 | <2 H | 0.05 | None |
| 44 | 62 | AML | C | T, OM | 3 W | 6 | 2 | 2 H | 0.05 | None |

Cancer: sal gland; salivary gland. AML; acute myelocytic leukemia. ALL acute lymphocityc leukemia. B cell L; B cell Lymphoma. L; Lymphoma. CML; chronic lymphocytic leukemia. MM; multiple myeloma. MDS; myelodysplastic syndrome.
TX (therapy): R; radiation. ITC; intrathecal chemotherapy. C; chemotherapy. Sct; stem cell transplant.
Location (of the lesions): SL; sublingual. L; lips. T; tongue. U; uvula. OP; oropharynx. P; palate. G; gums. OM; oral mucosa. D; diffuse. G; gingivae.
Length (duration of symptoms): M; months. W; weeks. D; days.
Pre-MB (before MB 0-10/10 numeric rating scale)
Post-MB (after MB 0-10/10 numeric rating scale)
Onset (of MB effect): d; days. h; hours.
MB %: dilution (concentration of the MB mix)

All of the patients reported pain at a level of 5 or greater on a 0-10 numeric rating scale, and the methylene blue oral rinse treatment resulted in almost of the patients having almost no pain (i.e., 0 on the rating scale) or a very low level of pain (i.e., 1 or 2 on the rating scale). For most of the patients, the onset of the effect of the methylene blue oral rinse ranged from less than 2 hours to up to 12 hours. In addition, an oral functioning score was measured in 3 categories ranging from 0-6 (eat, swallow, and talk; unable=2, difficulty=1, able=0). Therefore, the methylene blue oral rinse treatment was validated to decrease or completely relieve pain associated with oral mucositis. For patients that did not respond as robustly as others, it is possible that the active therapy may affect the effectiveness of the therapy.

Example 2—Validation of Methylene Blue Oral Rinse

A randomized double-blind, placebo-controlled trial comparing Methylene Blue oral rinse combined with conventional therapy and conventional therapy plus placebo in patients with intractable pain associated to oral mucositis is conducted to validate the findings in Example 1. The primary objective is to evaluate the efficacy of MB in reducing the severity of mucositis-related pain in cancer patients who underwent or are undergoing chemotherapy or radiation therapy. Patients are randomized to conventional therapy plus versus conventional therapy plus MB 0.25%, 0.5% or 1% oral rinse to swish and spit. This study design has two arms—three experimental arms with different concentrations and a control arm. The experimental arms are to receive 0.25%, 0.5% or 1% MB solution in addition to conventional therapy, and the control arm will receive conventional therapy. Patients are randomized as described below. Neither the physician nor the patient are aware of the group to which the patient is randomized.

Oral mucositis pain reduction (i.e., measured by using numeric rating scale NRS; 0 representing no pain to 10 representing the worst possible pain) and oral functioning (i.e., measured by the ability to swallow, eat and talk) are both scales included in the modified Harris mucositis-related pain assessment tool (MHMPAT). Both scales are measured immediately after administration and 1, 2, 7 and 21 days post administration of the oral rinse.

Secondary outcomes measured include duration of pain relief, the number of MB doses needed to achieve pain relief, the morphine equivalent daily dose (MEDD) used for oral mucositis pain, at 2, 7 and 21 days post administration, the incidence of untoward side effects immediately after administration and 1, 2, 7, 21 days, and a patient satisfaction score using a liker scale 1-5.

The MB oral rinse is prepared by diluting 5-10 mL of commercially available 10 mg/mL solution with 100-200 mL of water (Medicines Complete). The rinse is stored at 20° C. to 25° C. (68° F. to 77° F.) but may be exposed to temperatures ranging from 15° C. to 30° C. (59° F. to 86° F.). There is no need for light protection.

The inclusion criteria for the study is patients with a cancer diagnosis, receiving chemotherapy, radiation therapy or chemoradiation; a current diagnosis of oral mucositis; patients with pain associated with oral mucositis; age greater than 18 years; and voluntary written consent. The exclusion criteria was patients with known allergy to MB; patients taking medication with known significant drug interactions; pregnant or lactating patients; patients who are cognitively impaired and unable to consent for the study; patients with risk of broncho-aspiration based on documented swallowing test by Speech Pathologist (if available); and patients undergoing any other experimental intervention for oral mucositis.

Patients are recruited for the study through multiple care sites and patients with complaints consistent with mucositis will be screened for eligibility for enrollment in the study. Preparation and randomization of the study medication (MB or placebo) for each patient is performed by a compound research pharmacy. The study medication is available to the patient through the dispensing pharmacy along with instructions on how to take study medications.

The participants took MB or placebo solution via the oral swish and spit technique. They are instructed to take one mouth full (6-10 mL) of the solution to be held at the painful sites for five minutes then to swish and spit. The same steps are repeated every 6 hours as needed until the pain was controlled.

Patients enrolled in the study are to be completed a baseline assessment questionnaire in person, including the MHMPAT. The patient will have subsequent follow-up interviews at 1, 2, 7, 21 days with repeat assessment of the modified Harris mucositis-related pain assessment tool. The patient's medication use is also assessed at follow-up, including MEDD and other reported analgesic used for the treatment of their mucositis-related pain. Lastly, the research team investigate any side effects from the treatment.

All patients are monitored through weekly in person or by phone calls by the research staff allowing for close monitoring of potential adverse events during treatment. In addition, patients are given a contact phone number for treatment-related questions. Research staff collect toxicity, symptoms, and adherence to study medication schedule weekly. Treatment-related toxicities (NCI Common Terminology Criteria for Adverse Events, version 4) are monitored by the research staff.

Descriptive statistics (means (SDs) or counts (percent)) are used to summarize demographics, disease, and treatment variables according to the intervention arm. Potential differences between the arms (0.25%, 0.5% and 1% MB solution, and the conventional therapy) based on demographic, disease, and treatment variables will be explored using Chi-square test or two sample t-test, depending upon the nature of the variables being investigated. If the normality assumption is not met for the t-test, the Wilcoxon rank-sum test is used. When some of the expected values are small, Fisher's exact test is used instead of Chi-square test. A p-value of 0.05 is used to determine significance.

The primary endpoint is the change in pain scores assessed within the NRS component of the MHMPAT from baseline to 21 days. The mean change in scores is compared between 2 arms, utilizing one-way ANOVA. If there are significant differences between 2 arms in some covariates, a linear regression model is utilized to compare 2 arms by adjusting those significant covariates. The mean pain scores over time is compared between 2 arms, utilizing mixed effects models. Covariates that show significant differences between 2 arms will be adjusted in the mixed effects models.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
Breivik et al., Br J Anaesth. 101(1):17-24, 2008.
Chan et al., J. Oncol. Pharm. Pract. 11(4):139-143, 2005.
Duncan et al., Aliment. Pharmacol. Ther. 18(9):853-874, 2003.
Elting et al., Cancer 98(7):1531-1539, 2003.
Gremeau-Richard et al., Pain 108(102):51-57, 2004.
Harris et al., Ther Clin Risk Manag. 2(3):251-8, 2006.
Lalla and Peterson. Cancer J. 12(5):348-54, 2006.
Methylthioninium chloride. In: Martindale: The complete drug reference. London.
Pharmaceutical Press. From MedicinesComplete website. Accessed 2016 Aug. 16.
Okuno et al., J. Cancer Integr. Med. 2(3):179-183, 2004.
Peter et al., Eur J Clin Pharmacol 56:247-250, 2.
Peterson, J. Support Oncol. 4(2 Suppl. 1)9-13, 2.
Potting et al., Eur J Cancer Care (Engl) 15(5):431-439, 2.
Rengelshausen et al., Eur J Clin Pharmacol 60:709-715, 2004.
Rodríguez-Caballero e.g., Int J Oral Maxillofac Surg. 41(2): 225-238, 2012.
Saadeh, Pharmacotherapy 25(4):540-554, 2.
Saunders et al., Support Care Cancer 2013; 21(11):3191-3207, 2.
Shaiova et al., Support Care Cancer 12(4):268-273, 2.
Slatkin et al., Pain Med. 4(3):298-303, 2.
Sonis, Oral Oncol 45(12):1015-1020, 2009.
Stokman et al., Support Care Cancer 13(1):42-48, 2005.
Trotti et al., Radiother Oncol 66(3):253-262, 2003.
U.S. Pat. No. 4,961,926
U.S. Pat. No. 5,102,870
U.S. Pat. No. 5,545,668
U.S. Pat. No. 5,635,489
U.S. Pat. No. 5,945,089
U.S. Pat. No. 6,025,326
U.S. Pat. No. 6,828,308
U.S. Pat. No. 6,946,118
U.S. Patent Publication No. 2003/0236217
Walter-Sack et al., Eur J Clin Pharmacol 65:179-189, 2009.
Worthington et al., Cochrane Database Syst. Rev. 2:CD000978, 2006.

What is claimed is:

1. A method for treating cancer therapy-induced oral mucositis in a subject comprising selecting a subject having cancer and undergoing cancer therapy and administering to the oral mucosa of the subject a methylene blue oral rinse that is essentially free of chlorohexidine, in an amount effective to treat the oral mucositis, wherein the oral mucositis is not caused by herpes virus infection, herpangina, burns, tooth extraction, gingivitis, graft versus host disease or a microbial infection and the treatment is not to prevent oral mucositis.

2. The method of claim 1, wherein the subject is suffering from pain or oral lesions.

3. The method of claim 1, wherein the subject is in need of improving oral function-including improving the subject's ability to eat, swallow, and/or talk.

4. The method of claim 1, wherein the methylene blue oral rinse comprises 0.01% to 1% methylene blue.

5. The method of claim 1, wherein the methylene blue oral rinse comprises 0.05% to 0.2% methylene blue.

6. The method of claim 1, wherein the methylene blue oral rinse comprises 0.025% to 0.05% methylene blue.

7. The method of claim 1, wherein the methylene blue oral rinse comprises a saline solution.

8. The method of claim 1, wherein administering comprises performing an oral swish and spit technique.

9. The method of claim 8, wherein the oral swish and spit technique comprises taking 6 to 10 mL of the oral rinse in the mouth and holding the oral rinse at painful sites for at least 5 minutes before swishing and spitting.

10. The method of claim 2, wherein pain is measured using a numeric rating scale and/or oral functioning scale.

11. The method of claim 10, wherein the pain and/or lesions are decreased by at least 50% as compared to pain and/or lesions prior to administering the methylene blue oral rinse.

12. The method of claim 10, wherein the pain and/or lesions are essentially completely relieved.

13. The method of claim 1, wherein the subject has received or is undergoing chemotherapy, hematopoietic stem cell transplantation, bone marrow transplantation, and/or radiotherapy.

14. The method of claim 1, wherein the subject has head and neck cancer, thyroid cancer, oral cancer, salivary gland cancer, acute myelocytic leukemia, acute lymphocytic leukemia, B cell lymphoma, chronic lymphocyte leukemia, or multiple myeloma.

15. The method of claim 1, wherein administering is every 48 hours, every 24 hours, every 12 hours, or every 6 hours.

16. The method of claim 1, wherein the oral rinse further comprises an analgesic.

17. The method of claim 1, wherein the cancer therapy-induced oral mucositis is chemotherapy-induced oral mucositis.

18. The method of claim 1, wherein the cancer therapy-induced oral mucositis is radiation-induced oral mucositis.

19. The method of claim 1, wherein treating comprises relieving pain.

20. The method of claim 1, wherein the oral rinse is essentially free of zinc sulfate.

* * * * *